United States Patent
Koss et al.

(10) Patent No.: US 10,843,989 B2
(45) Date of Patent: Nov. 24, 2020

(54) METHOD FOR THE COMBINED PRODUCTION OF METHANOL AND AMMONIA

(71) Applicant: GasConTec GmbH, Bad Homburg v. d. Höhe (DE)

(72) Inventors: Ulrich Koss, Bad Homburg vor der Höhe (DE); Dierk Mueller, Karben (DE); Ulrich Wagner, Bernburg (DE)

(73) Assignee: GasConTec GmbH

( * ) Notice: Subject to any disclaimer, the term of this patent is extended or adjusted under 35 U.S.C. 154(b) by 0 days.

(21) Appl. No.: 16/461,028

(22) PCT Filed: Nov. 16, 2017

(86) PCT No.: PCT/EP2017/079483
§ 371 (c)(1),
(2) Date: May 15, 2019

(87) PCT Pub. No.: WO2018/091593
PCT Pub. Date: May 24, 2018

(65) Prior Publication Data
US 2019/0308919 A1    Oct. 10, 2019

(30) Foreign Application Priority Data

Nov. 16, 2016   (EP) ..................... 16199136
May 2, 2017     (EP) ..................... 17169058

(51) Int. Cl.
| | | |
|---|---|---|
| *C07C 29/151* | (2006.01) | |
| *C01B 3/02* | (2006.01) | |
| *C01B 3/38* | (2006.01) | |
| *C01C 1/04* | (2006.01) | |
| *C10L 1/02* | (2006.01) | |
| *C10L 1/04* | (2006.01) | |
| *C10K 3/04* | (2006.01) | |
| *C01B 13/02* | (2006.01) | |
| *C10K 1/16* | (2006.01) | |
| *C01B 3/50* | (2006.01) | |

(52) U.S. Cl.
CPC .......... *C07C 29/1518* (2013.01); *C01B 3/025* (2013.01); *C01B 3/382* (2013.01); *C01B 3/50* (2013.01); *C01B 13/0203* (2013.01); *C01C 1/0488* (2013.01); *C10K 1/165* (2013.01); *C10K 3/04* (2013.01); *C10L 1/02* (2013.01); *C10L 1/04* (2013.01); *C01B 2203/0244* (2013.01); *C01B 2203/0283* (2013.01); *C01B 2203/043* (2013.01); *C01B 2203/0415* (2013.01); *C01B 2203/061* (2013.01); *C01B 2203/068* (2013.01); *C10L 2200/04* (2013.01); *C10L 2200/0423* (2013.01); *Y02P 20/52* (2015.11)

(58) Field of Classification Search
CPC ............ C07C 29/1516; C07C 29/1518; C07C 29/152; C07C 31/04; C01B 3/025; C01B 2203/061; C01B 2203/0244; C01B 2203/1235; C01B 2203/1258; C01B 2203/068; B01J 2219/00006; C01C 1/0488
See application file for complete search history.

(56) References Cited

U.S. PATENT DOCUMENTS

| | | | |
|---|---|---|---|
| 5,180,570 A | 1/1993 | Lee et al. | |
| 2012/0148472 A1 | 6/2012 | Ahmed et al. | |
| 2017/0152219 A1* | 6/2017 | Mabrouk | .............. C01B 3/48 |

FOREIGN PATENT DOCUMENTS

| | | |
|---|---|---|
| DE | 102004013539 A1 | 10/2005 |
| EP | 0011404 A1 | 5/1980 |
| WO | 2012110339 A1 | 8/2012 |
| WO | 2016132092 A1 | 8/2016 |

OTHER PUBLICATIONS

International Search Report for Application No. PCT/EP2017/079483, dated Feb. 6, 2018, 7 pages.
Written Opinion for Application No. PCT/EP2017/079483, dated Feb. 6, 2018, 6 pages.

* cited by examiner

*Primary Examiner* — Jafar F Parsa
(74) *Attorney, Agent, or Firm* — McCarter & English, LLP

(57) ABSTRACT

Method and system for the combined production of methanol and of ammonia, and method for producing a fuel using methanol, wherein a carbon-containing energy carrier flow and an oxygen flow from an oxygen-producing assembly are fed to a synthesis gas reactor assembly for obtaining a synthesis gas flow with hydrogen and carbon oxides, wherein the synthesis gas flow is fed to a methanol reactor assembly for the partial conversion into methanol, and wherein, from the methanol reactor assembly, a residual gas flow is obtained from which a hydrogen-containing flow is obtained, which is at least partially fed to an ammonia reactor assembly and at least partially converted into ammonia there. In an enrichment step, the molar fraction of hydrogen in the synthesis gas flow obtained from the synthesis gas reactor assembly is increased relative to the molar fraction of carbon oxides prior to the feeding to the methanol reactor assembly.

13 Claims, 1 Drawing Sheet

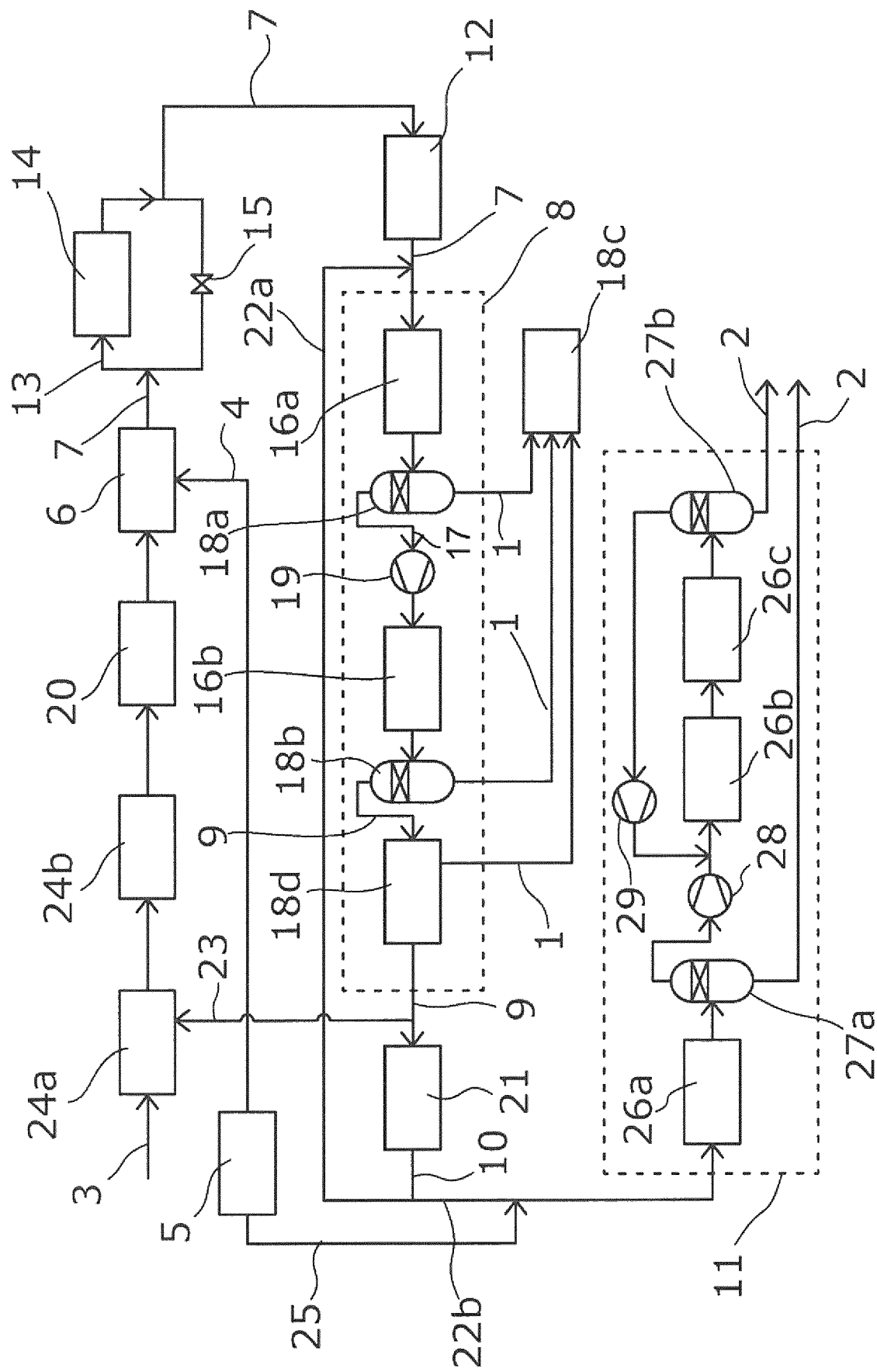

METHOD FOR THE COMBINED PRODUCTION OF METHANOL AND AMMONIA

CROSS-REFERENCE TO RELATED APPLICATIONS

This application is a national stage application of international application no. PCT/EP2017/079483 filed Nov. 16, 2017, entitled "Method for the Combined Production of Methanol and Ammonia," claiming priority to European application no. EP 17169058.9A filed May 2, 2017, and European patent application no. EP 16199136.9 filed Nov. 16, 2016, which are hereby expressly incorporated by reference as part of the present disclosure.

FIELD OF THE INVENTION

The present disclosure generally relates to a method and a system for the combined production of methanol and ammonia and a method for producing a fuel.

BACKGROUND

Various approaches for the combined production of methanol and ammonia are known from the prior art. The published patent application EP 0 011 404 describes an integrated method for producing methanol and ammonia in which a synthesis gas with hydrogen, carbon oxide and nitrogen is produced, which is then fed to a methanol synthesis. Remaining carbon oxides are removed from the residual gas, so that a flow with nitrogen and hydrogen is obtained, which flow is fed to an ammonia synthesis. However, this approach is disadvantageous in that the nitrogen carried along in the methanol synthesis not only requires compressors and reactors with large dimensions, which reduces economic viability, but that unwanted substances, such as triethylamine, are also produced in the process.

The published patent application DE 10 2004 013 539 A1 also describes a method for co-producing methanol and ammonia. Here, the synthesis gas is obtained by catalytic partial oxidation with oxygen from an air separation unit, so that the considerable nitrogen content in the methanol synthesis is eliminated. This synthesis gas is then respectively fed to respective reactor assemblies for methanol synthesis and ammonia synthesis which, with respect to the process, are arranged in parallel. In this case, it is disadvantageous that complex equipment for the removal of methane as well as of argon and remaining carbon monoxide is required upstream of the reactor assembly for ammonia synthesis, i.e., specifically, a low-temperature separation means, which affects economic viability.

The patent specification U.S. Pat. No. 5,180,570, also describes an integrated process for producing methanol and ammonia from a carbon-containing energy carrier flow. The synthesis gas is obtained in a multi-stage reformer assembly with conventional steam reforming and downstream autothermic reforming while oxygen is being supplied. This prior art is disadvantageous in that steam reforming, which causes the methane to be split with water into a hydrogen-rich synthesis gas for reaching the required hydrogen surplus in methanol synthesis, can only be carried out at comparatively low pressures. Therefore, a complex compression of the entire synthesis gas prior to methanol synthesis is necessary. Moreover, no sufficiently comprehensive conversion of the carbons into methanol is achieved in single-stage methanol synthesis, which is why both a compression of unreacted recycled gas and a low-temperature scrubbing of the residual gas prior to ammonia synthesis is necessary. Both actions considerably increase the effort.

SUMMARY

It is an object to provide a method for the combined production of methanol and of ammonia which is more economical.

The object is achieved, in at least some embodiments, by a method for the combined production of methanol and of ammonia comprises the steps of feeding a carbon-containing energy carrier flow and an oxygen flow from an oxygen-producing assembly to a synthesis gas reactor assembly, obtaining a synthesis gas flow with hydrogen and carbon oxides from the synthesis gas reactor assembly, feeding the synthesis gas flow to a methanol reactor assembly for the partial conversion into methanol, obtaining a residual gas flow from the methanol reactor assembly, obtaining a hydrogen-containing flow from the residual gas flow, at least partially feeding the hydrogen-containing flow to an ammonia reactor assembly, at least partially converting the hydrogen-containing flow into ammonia in the ammonia reactor assembly, and performing an enrichment step, including: increasing the molar fraction of hydrogen in the synthesis gas flow obtained from the synthesis gas reactor assembly relative to the molar fraction of carbon oxides prior to the feeding to the methanol reactor assembly. In at least some embodiments, the methanol can be used to produce a fuel.

The object is achieved, in at least some embodiments, by a system for the combined production of methanol and of ammonia, comprising an oxygen-producing assembly configured to obtain an oxygen flow, a synthesis gas reactor assembly configured to obtain a synthesis gas flow with hydrogen and carbon oxides from a carbon-containing energy carrier flow and the oxygen flow, a methanol reactor assembly configured to partially convert the synthesis gas flow into methanol and to obtain a residual gas flow, an ammonia reactor assembly configured to at least partially receive a hydrogen-containing flow obtained from the residual gas flow, and configured to at least partially convert the hydrogen-containing flow into ammonia, and an enrichment assembly configured to increase the molar fraction of hydrogen in the synthesis gas flow obtained from the synthesis gas reactor assembly relative to the molar fraction of carbon oxides.

The inventors realized that the insufficient fraction of hydrogen produced in the synthesis gas production under high pressure with oxygen—which is insufficient even for methanol synthesis—may be compensated by being able to enrich the hydrogen fraction in the synthesis gas after producing the synthesis gas, but prior to feeding the synthesis gas to methanol synthesis. This enrichment makes the very complex and elaborate steam reforming stage dispensable, which is conventionally required for providing a hydrogen quantity in the synthesis gas flow that is sufficient for methanol synthesis and for ammonia synthesis.

Because the steam reforming stage is omitted, both the synthesis gas production itself and the above enrichment—be it the supply of hydrogen or the removal of carbon oxides—may in turn take place at pressure conditions due to which compression prior to methanol synthesis may be omitted or, in any case, be dimensioned smaller. Furthermore, due to the above enrichment, it is possible to achieve such a comprehensive conversion of carbon monoxide in the methanol synthesis, already in a single cycle, that the necessity for a recycling compressor in the methanol synthesis is eliminated. The factors that are regularly most important for the economic viability of methanol synthesis can be optimized in this way.

In at least one embodiment, the hydrogen is enriched by at least partially removing carbon dioxide from the synthesis gas flow. For this not only directly increases the molar fraction of hydrogen, but equally also reduces the consumption of hydrogen in the methanol synthesis by carbon dioxide.

Other embodiments involve shifting the relative weighting of methanol production on the one hand, and ammonia production on the other hand.

At least some embodiments comprise a two-stage methanol synthesis, which is suitable for achieving a comprehensive conversion of the carbon monoxide into the methanol already with a single cycle—also referred to as "once through" operation. The arrangement of the booster compressor between the methanol synthesis stages may dispense with compression prior to ammonia synthesis.

At least some embodiments involve autothermic reforming for obtaining the synthesis gas flow.

At least some embodiments involve the use of a pressure swing adsorption system for obtaining a purer hydrogen flow from the residual gas of the methanol synthesis.

This summary is not exhaustive of the scope of the present aspects and embodiments. Thus, while certain aspects and embodiments have been presented and/or outlined in this summary, it should be understood that the present aspects and embodiments are not limited to the aspects and embodiments in this summary. Indeed, other aspects and embodiments, which may be similar to and/or different from, the aspects and embodiments presented in this summary, will be apparent from the description, illustrations, and/or claims, which follow.

It should also be understood that any aspects and embodiments that are described in this summary and do not appear in the claims that follow are preserved for later presentation in this application or in one or more continuation patent applications.

BRIEF DESCRIPTION OF THE DRAWINGS

Other details, features, goals and advantages are explained below with reference to the drawing, which shall be understood not to be limiting and which will be explained below with reference to the drawing. In the drawing:

FIG. 1 is a schematic flow chart of a system for the combined production of methanol and ammonia.

DETAILED DESCRIPTION

The system shown in FIG. 1 serves for the combined production of methanol 1 and ammonia 2, and is also configured for carrying out a method for the combined production of methanol 1 and ammonia 2.

In the method for the combined production of methanol 1 and of ammonia 2, according to at least some embodiments, a carbon-containing energy carrier flow 3, such as a natural-gas flow, and an oxygen flow 4 from an oxygen-producing assembly 5 are fed to a synthesis gas reactor assembly 6 for obtaining a synthesis gas flow 7. This oxygen-producing assembly 5 is an, in principle arbitrary, system or device which obtains molecular oxygen, for example, from a fluid—i.e. from a liquid or a gas, or from a mixture of liquids or a mixture of gases. In at least some embodiments, this may be carried out by an oxygen-containing fluid being split into its constituents. In at least some such embodiments, this oxygen-producing assembly 5—as in the exemplary embodiment of FIG. 1—may be an air separation unit (ASU) for obtaining molecular oxygen from the air.

Both this oxygen-producing assembly 5 and the synthesis gas reactor assembly 6 are included in the system for the combined production of methanol 1 and of ammonia 2 in at least some embodiments. Since it is obtained from the oxygen-producing assembly 5, the oxygen flow 4 has oxygen as its predominant constituent. In any case, the oxygen fraction of the oxygen flow 4 exceeds that of the ambient air, and the nitrogen fraction of the oxygen flow 4 is less than that of the ambient air. In at least some embodiments, the oxygen fraction of the oxygen flow 4 is at least 80%, or at least 90%, or at least 95%. It may also be that the oxygen flow 4 substantially consists of oxygen, wherein small fractions of, for example, nitrogen and noble gases possibly may be present in the oxygen flow 4.

According to at least some embodiments, the synthesis gas flow 7 includes hydrogen and carbon oxide, i.e. carbon monoxide and carbon dioxide. In this case, the synthesis gas flow 7 may be obtained from the oxygen-producing assembly 5 with methods for synthesis gas production while supplying an oxygen flow 4 known from the prior art. The type of synthesis gas production, for at least some embodiments, is described below. In addition, the synthesis gas flow 7 may also contain small fractions of other substances, such as methane, nitrogen and noble gas, with a respective molar fraction of less than 10% in at least some embodiments.

According to the method according to at least some embodiments, the synthesis gas flow 7 is fed to a methanol reactor assembly 8 for the partial conversion into methanol 1, and a residual gas flow 9 is obtained from the methanol reactor assembly 8. The partial conversion into methanol 1 may be, for example, catalytic. The residual gas flow 9 may include methanol as well as unreacted constituents of the synthesis gas flow 7, i.e. hydrogen and carbon oxides in at least some embodiments. The methanol reactor assembly 8 is also included in the system according to at least some embodiments. The method according to some such embodiments then further provides that a hydrogen-containing flow 10 is obtained from the residual gas flow 9, which hydrogen-containing flow 10 is at least partially—or, in some embodiments, substantially completely—fed to an ammonia reactor assembly 11, which is also included in the system according to at least some embodiments, and there is at least partially—for example substantially completely—converted into ammonia 2. The conversion into ammonia 2 may also be catalytic.

The method according to at least some embodiments is characterized in that, in an enrichment step, the molar fraction of hydrogen in the synthesis gas flow 7 obtained from the synthesis gas reactor assembly 6 is increased in relation to the molar fraction of carbon oxides prior to the feeding to the methanol reactor assembly 8. In other words, the molar fraction of hydrogen in the synthesis gas flow 7, in relation to the molar fraction of the carbon oxides in the synthesis gas flow 7, is larger after the enrichment step, which, with respect to the process, takes place between the synthesis gas reactor assembly 6 and the methanol reactor assembly 8, than prior to the enrichment step.

In principle, this enrichment of hydrogen in the synthesis gas flow 7—which relates to the molecular hydrogen ($H2$)—may take place in any manner. On the one hand, additional hydrogen may be fed into the synthesis gas flow 7. Accordingly, in at least some embodiments, the molar fraction of hydrogen is increased by—or, in some embodiments, only by—hydrogen being fed into the synthesis gas flow 7.

On the other hand, carbon oxides may also be removed from the synthesis gas flow 7. Accordingly, in at least some embodiments, the molar fraction of hydrogen is increased by—or, in some embodiments, only by—an at least partial removal of carbon oxides—e.g., carbon monoxide and/or carbon dioxide—from the synthesis gas flow 7.

A configuration, according to at least some embodiments, provides that carbon dioxide is at least partially removed from the synthesis gas flow 7 in the enrichment step. Consequently, the molar quantity of the hydrogen synthesis gas flow 7 is not increased, but only its molar fraction. This is reflected by a significant increase in the stoichiometric number from far below 2 to far above 3. For this purpose, in at least some embodiments, at least a partial flow of the synthesis gas flow 7—for example, according to the proposed system of FIG. 1, the substantially entire synthesis gas flow 7—may be fed to a carbon dioxide scrubbing 12—which may be an assembly for carbon dioxide scrubbing of the system according to the proposal—for at least partially removing the carbon dioxide. In this case, scrubbing can be carried out in any manner known per se from the prior art.

According to at least some embodiments, the carbon dioxide is removed from the synthesis gas flow 7 by chemical scrubbing in the enrichment step, and for example, in the carbon dioxide scrubbing 12. This may include chemical scrubbing in each case with piperazine-activated methyldiethanolamine, with simple methyldiethanolamine, with an aqueous ammonia solution or with an aqueous soda solution. According to at least some embodiments, the carbon dioxide is removed from the synthesis gas flow 7 by a physically absorbing absorbent in the enrichment step. In at least some such embodiments, the physically absorbing absorbent is cold methanol, Selexol or N-methyl-2-pyrrolidone (NMP). In the event the physically absorbing absorbent is cold methanol, this may be methanol obtained from the methanol reactor assembly 8.

It is not necessary to achieve a particular degree of purity in the above carbon dioxide scrubbing 12. Therefore, carbon dioxide scrubbing 12—for example, in the event a physically absorbing absorbent is employed—may be also configured without steam-driven regeneration. Therefore, in at least some embodiments, the carbon dioxide scrubbing 12 has a depressurization-based regeneration stage. In other words, a washing agent of the carbon dioxide scrubbing 12 is regenerated by means of depressurization.

In at least some embodiments, the synthesis gas flow 7 fed to the methanol reactor assembly 8—i.e. the synthesis gas flow 7 after the enrichment step—has a molar fraction of carbon dioxide of up to 3%. Consequently, the molar fraction of carbon dioxide in the synthesis gas flow 7 is reduced to a value that is significantly lower than in conventional carbon dioxide scrubbing.

In principle, the enrichment step may consist only of the above removal of carbon dioxide by carbon dioxide scrubbing 12. This approach is advantageous for methanol synthesis because carbon dioxide consumes more hydrogen in methanol synthesis than carbon monoxide. If the ratio of production of methanol to ammonia is to shift more towards ammonia, the enrichment step, however, may alternatively or additionally comprise other measures for enriching hydrogen. At least some embodiments provide that in the enrichment step, at least one—or, in some embodiments, further—partial flow 13 of the synthesis gas flow 7 is fed to a shift conversion 14, in which carbon monoxide is at least partially converted into hydrogen and carbon dioxide by a reaction with water vapor. Since as a result of this reaction the number of carbon oxide molecules remains constant—even though a carbon monoxide molecule becomes a carbon dioxide molecule—and the number of hydrogen molecules increases at the same time, the molar fraction of hydrogen also increases as a result. The synthesis gas flow 7 may also be fed to the shift conversion 14 substantially as a whole. The process occurring in the shift conversion 14 is also referred to as a water-gas shift reaction. Consequently, the shift conversion 14, which may be included in the system according to at least some embodiments, may also be referred to as a device for a water-gas shift reaction. This water-gas shift reaction also leads to an increase in the molar fraction of hydrogen in the synthesis gas flow 7, as compared to the molar fraction of carbon oxides.

Further, in at least some embodiments—in accordance with the illustration in FIG. 1—the branching-off of the partial flow 13 to the shift conversion 14, with respect to the process, is arranged upstream of the carbon dioxide scrubbing 12. Accordingly, the partial flow 13 fed to the shift conversion 14 may be subsequently fed to the carbon dioxide scrubbing 12. In this way, the carbon dioxide produced in the water-gas shift reaction may be washed out again in the carbon dioxide scrubbing 12. Thus, a dual increase of the molar fraction of hydrogen occurs. In the shift conversion 14, in at least some embodiments, the shift conversion 14 substantially exclusively carries out a high-temperature water-gas shift reaction, e.g., at at least 450°. In this way, a separate stage for a low-temperature water-gas shift reaction may be omitted.

The change of the respective molar fractions of hydrogen, carbon monoxide and carbon dioxide in the synthesis gas flow 7 caused by the water-gas shift reaction and the subsequent carbon dioxide scrubbing 12 influences both the conversion into methanol 1 in the methanol reactor assembly 8 and the conversion into ammonia 2 in the ammonia reactor assembly 11. In at least some embodiments, the molar fraction in the synthesis gas flow 7 of the, for example, further, partial flow 13 fed to the shift conversion 14 consequently can be adapted for adjusting the ratio of the methanol 1 obtained by conversion and the ammonia 2 obtained by conversion. For this purpose, the system according to at least some embodiments may include the control valve 15 shown in FIG. 1 for adjusting this ratio.

However, in a first embodiment of the method for the combined production of methanol 1 and of ammonia 2—implemented here by FIG. 1—and in all specifications of quantity below, which are associated with at least some such embodiments of the method, no partial flow 13 is branched off to the shift conversion 14. Rather, the control valve 15 is set such that as much methanol as possible is produced in relation to ammonia, and thus the substantially entire synthesis gas flow 7 is made to bypass the shift conversion 14. If the above ratio is to be shifted in favor of ammonia, a correspondingly larger fraction of the synthesis gas flow 7 can be fed to shift conversion 14 as a partial flow 13.

In this first embodiment of the method for the combined production of methanol 1 and ammonia 2, the synthesis gas flow 7 fed to the methanol reactor assembly 8—i.e. after an optional shift conversion 14, which has not taken place in this case, and carbon dioxide scrubbing 12—substantially has a respective molar fraction of 68% hydrogen, 24% carbon monoxide, 2% carbon dioxide, 2% methane, 2% water and 1% nitrogen, at a pressure of substantially 77 bars and a temperature of 40° C. In this case, the contribution of a possibly returned hydrogen partial flow 22a—which will be described below—is not taken into account. Thus, this is the synthesis gas flow 7 which, with respect to the process, is arranged directly downstream of the carbon dioxide scrubbing 12.

This enrichment of the molar fraction of hydrogen in the synthesis gas flow 7, which is obtained by the measures described above for example, makes it possible to attain an extensive conversion of the carbon monoxide in the methanol reactor assembly 8. For example, carbon monoxide in the synthesis gas flow 7 fed to the methanol reactor assembly 8 may be substantially completely converted into methanol 1, so that the molar fraction of carbon monoxide in the residual gas flow 9 is 4% at most. In at least some embodiments of the method for the combined production of methanol 1 and ammonia 2, the residual gas flow 9—for example, prior to being fed to the pressure swing adsorption system 21 to be described below—substantially has a respective molar fraction of 90% hydrogen, 4% carbon monoxide, 1% carbon dioxide, 2% methane, 1% water and 1% nitrogen, at a pressure of substantially 87 bars and a temperature of 43° C.

In principle, the methanol reactor assembly 8 may be configured in any way. In accordance with the illustration in FIG. 1—the methanol reactor assembly 8 has a first reactor stage 16a for the, in, for example, catalytic, synthesis of methanol 1 and a second reactor stage 16b for the, in, for example, catalytic, synthesis of methanol 1, that the synthesis gas flow 7 fed to the methanol reactor assembly 8 is fed to the first reactor stage 16a, and that an unreacted residual gas 17 from the first reactor stage 16a is fed to the second reactor stage 16b. For the above-mentioned high degree of conversion into methanol 1, it the molar ratio in the first reactor stage 16a given by S in accordance with the formula $S=(n(H2)-n(CO2))/(n(CO)+n(CO2))$, with n in [mol], of at least 2.5, for example, of at least 3.5, may be obtained. This molar ratio is also referred to as the stoichiometric number. The stoichiometric number can be increased by removal of carbon dioxide in carbon dioxide scrubbing 12—if need be, in combination with an upstream shift conversion 14.

In principle, both the first reactor stage 16a and the second reactor stage 16b can be configured in any manner. In at least some embodiments, however, one or both of the reactor stages 16a, b are cooled. In at least some embodiments, a first fluid—e.g. water—is thus fed to the first reactor stage 16a for cooling it and, alternatively or additionally, a second fluid, which may also be water, is fed to the second reactor stage 16b for cooling it. Thus, the first reactor stage 16a may be operated isothermally and, alternatively or additionally, the second reactor stage 16b may be operated isothermally. In at least some such embodiments, the isothermal operation of both reactor stages 16a, b—which corresponds to the exemplary embodiment shown in FIG. 1—enables a synthesis of methanol 1 in both reactor stages 16a, b that is approximately identical with respect to quantity. Thus, between 30% and 70%, or between 40% and 60%, of the molar quantity of methanol 1 obtained in the methanol reactor assembly 8 by conversion may be produced in the first reactor stage 16a, and the rest of the molar quantity of methanol 1 obtained in the methanol reactor assembly 8 by conversion may be produced in the second reactor stage 16b.

In the first embodiment of the proposed method for the combined production of methanol 1 and ammonia 2, a mass flow of 94,962 kg/h of methanol 1 is obtained from a first condensation stage 18a—which is to be described below—and a mass flow of, in total, approx. 72,043 kg/h of methanol 1 is obtained from a second condensation stage 18b and a scrubber device 18d—which are also described below. The total result is a mass flow of obtained methanol 1 of methanol 1 from the condensation stages 18a, b and the scrubber device 18d of 167,005 kg/h. This methanol 1 is first obtained in the process as a part of the respective crude-methanol flow, which crude-methanol flow may also include a certain fraction of water. Even if these two numbers specified above cannot be necessarily assigned to the reactor stages 16a, b on a one-to-one basis, a substantially existing balance is nevertheless recognizable. Other relevant specifications of quantity regarding these embodiments follow below. In contrast, conventional dual-stage reactor assemblies for methanol synthesis are regularly characterized in that significantly less methanol is converted in the respective downstream reactor stage.

Due to the large quantity of obtained methanol 1 in the two reactor stages 16a, b, it becomes possible to let the carbon oxides of the synthesis gas flow 7 pass through both reactor stages 16a, b only once.

Accordingly, in at least some embodiments, the unreacted residual gas 17 fed to the second reactor stage 16b substantially includes all unreacted carbon oxides from the first reactor stage 16a. Therefore, there are substantially no unreacted carbon oxides from the unreacted residual gas 17 that are returned to the first reactor stage 16a. In other words, carbon oxides of the synthesis gas flow 7 pass through the first reactor stage 16a only once. A recycling compressor for methanol synthesis of any consequence can thus be omitted. However, this not only means dispensing with the recycling compressor as such, but also makes it possible to downsize the methanol reactor assembly 8 or of its reactor stages 16a, b, because the material volumes can, as a whole, be reduced considerably due to the lack of circulation through the recycling compressor.

Advantageously, such a passage, which takes place only once, also applies to the second reactor stage 16b. The corresponding embodiments, which also corresponds to the illustration of FIG. 1, are characterized in that the residual gas flow 9 substantially includes all unreacted carbon oxides from the second reactor stage 16b. Note that the hydrogen-containing flow 10 is obtained from the residual gas flow 9. In other words, there are substantially no unreacted carbon oxides from the second reactor stage 16b that have to be returned to any one of the two reactor stages 16a, b. In at least some embodiments, carbon oxides pass through the second reactor stage 16b only once.

A removal of methanol 1 between the two reactor stages 16a, b is also extremely advantageous for improving the methanol conversion in the second reactor stage 16b. Therefore, in at least some embodiments, with respect to the process, a first condensation stage 18a for the separation of methanol 1 converted in the first reactor stage 16a and for obtaining the unreacted residual gas 17 from the first reactor stage 16a is arranged downstream of the first reactor stage 16a. This first condensation stage 18a is included in the methanol reactor assembly 8. In the process, the methanol 1—as mentioned above—can be separated as a crude methanol, which may then be fed to a distillation device 18c for obtaining pure methanol, which distillation device 18c is also included in the system according to the proposal. In the first embodiment of the proposed method for the combined production of methanol 1 and ammonia 2, a pure-methanol flow substantially consisting of methanol with a mass flow of 166,785 kg/h is obtained from the distillation device 18c, wherein the small difference of this mass flow of methanol to the sum of the above-mentioned mass flows can be explained by losses.

For removing methanol 1 also from the second reactor stage 16b, in at least some embodiments, it is provided that, with respect to the process, a second condensation stage 18b for the separation of methanol 1 converted in the second reactor stage 16b and for obtaining the residual gas flow 9 from the second reactor stage 16b is arranged downstream of the second reactor stage 16b. The second condensation stage 18b is also included in the methanol reactor assembly 8, and the methanol 1 can also be separated as a crude methanol here, which—as shown in FIG. 1—is fed to the above distillation device 18c. Finally, the residual gas flow 9 can also be subjected to scrubbing for washing out methanol 1 in a scrubber device 18d, which is in this case also included in the methanol reactor assembly 8.

As will be explained in more detail below, a compressor forward of the methanol reactor assembly 8 can advantageously be omitted. In order also to avoid a compressor between the methanol reactor assembly 8 and the ammonia reactor assembly 11, a compressor may be disposed between the reactor stages 16a, b—as shown in FIG. 1. Therefore, in at least some embodiments, the unreacted residual gas 17 from the first reactor stage 16a is fed to a booster compressor 19 for increasing pressure prior to feeding it to the second reactor stage 16b. In at least some such embodiments, the booster compressor 19 provides an ammonia synthesis pressure with which the hydrogen-containing flow 10 is fed to the ammonia reactor assembly 11. As an example, this ammonia synthesis pressure may be 90 bars. In other words, the pressure with which the hydrogen-containing flow 10 is fed to the ammonia reactor assembly 11 is caused by the booster compressor 19, so that therefore, no other device for increasing pressure is disposed, with respect to the process, between the booster compressor 19 and the ammonia reactor assembly 11. Thus, the otherwise commonly used recycling compressor in a methanol system is converted into a synthesis gas compressor for the ammonia process.

Ammonia synthesis pressure means a pressure of the hydrogen-containing flow 10 which is sufficient for the, for example, catalytic, conversion into ammonia 2. In this case, it is sufficient if only a small fraction of the hydrogen-containing flow 10 is converted into ammonia 2 at this ammonia synthesis pressure. In at least some embodiments, it may be—as will be described in more detail below—that after the feeding to the ammonia reactor assembly 11 at this comparatively low pressure, subsequent to passing through a first reactor stage in the ammonia reactor assembly 11, the remaining substance from the hydrogen-containing flow 10 is compressed to a higher pressure within the ammonia reactor assembly 11 for ammonia synthesis. Providing this ammonia synthesis pressure by a pressure increase of the unreacted residual gas 17 by means of the booster compressor 19—and therefore an indirect pressure increase of the hydrogen obtained only downstream in the process—may be shrewd because a direct compression of substantially pure hydrogen is practically hardly possible. In at least some embodiments, the booster compressor 19 increases the unreacted residual gas 17 to an ammonia synthesis pressure of at least 60 bars, for example, to an ammonia synthesis pressure between 70 bars and 120 bars. In this case, it is not necessary that this pressure level is continuously maintained up to the ammonia reactor assembly 11 by the booster compressor 19; rather, a certain pressure loss until then is possible.

Again describing the obtaining of the synthesis gas flow 7, it is provided, in at least some embodiments, that the synthesis gas flow 7 is obtained in the synthesis gas reactor assembly 6 by autothermic reforming with the oxygen flow 4 as an oxidant. In autothermic reforming, which is known per se from the prior art, a catalytic partial oxidation—in this case by means of the oxygen flow 4—provides the heat required for the endothermic steam reforming reactions. The reforming of methane is endothermic.

It is known that autothermic reforming results in a stoichiometric number of less than 2, so that as such, it is not suitable for reaching the ranges for the stoichiometric number proposed above. Surprisingly, however, it has proved advantageous to provide a hydrogen enrichment for increasing the stoichiometric number prior to the feeding to the methanol reactor assembly 8, because a synthesis gas compressor prior to methanol synthesis may be omitted due to the possible operation of the autothermic reforming at higher pressures. Accordingly, in at least some embodiments, the synthesis gas reactor assembly 6 provides a methanol synthesis pressure with which the synthesis gas flow 7 is fed to the methanol reactor assembly 8. Analogously to the statements regarding the above booster compressor 19, this means that the pressure with which the synthesis gas flow 7 is fed to the methanol reactor assembly 8 is caused by the synthesis gas reactor assembly 6, so that therefore, no other device for increasing pressure is disposed, with respect to the process, between the synthesis gas reactor assembly 6 and the methanol reactor assembly 8. Methanol synthesis pressure means a pressure of the synthesis gas flow 7 which is sufficient for the, for example, catalytic, conversion into methanol 1. This methanol synthesis pressure may be about 80 bars.

In this respect, in at least some embodiments, the synthesis gas reactor assembly 6 is operated with a pressure of between 60 bars and 110 bars. As a rule, this is not useful if steam reforming is also used for synthesis gas production. As is shown in FIG. 1, the carbon-containing energy carrier flow 3, prior to being fed to the synthesis gas reactor assembly 6, is fed to a pre-reformer 20 for splitting hydrocarbons with at least two carbon atoms. In particular, they are split into methane, hydrogen and carbon oxides. The pre-reformer 20 is also included, in at least some embodiments, in the system. Such a pre-reforming performed by the pre-reformer 20 is known from the prior art as steam reforming at low temperature, wherein, as is also known, the methanation reaction and the water-gas shift reaction are substantially in equilibrium in the pre-reformer 20. Possible hydrocarbons with at least two carbon atoms include ethane, propane, butane and pentane. However, the use of such a pre-reformer which, in contrast to a steam reformer, does not have to be heated, does not limit the pressure conditions substantially—also in contrast to the steam reformer.

In the first embodiment of the method for the combined production of methanol 1 and ammonia 2, the carbon-containing energy carrier flow 3 prior to being fed to the pre-reformer 20 substantially has a respective molar fraction of 63% of methane and of 25% of water, wherein the rest is substantially formed by ethane and propane. Then, the carbon-containing energy carrier flow 3 fed from the pre-reformer 20 to the synthesis gas reactor assembly 6—for example, due to the supply of water vapor in the pre-reformer 20—in some such embodiments of the method for the combined production of methanol 1 and ammonia 2 substantially has a respective molar fraction of 53% of water, 36% of methane, 7% of hydrogen and 3% of carbon dioxide, at a pressure of substantially 81 bars and a temperature of 645° C. In at least some embodiments of the method for the combined production of methanol 1 and ammonia 2, the mass flow of the carbon-containing energy carrier flow at this point is 371,732 kg/h.

In at least some embodiments, the carbon-containing energy carrier flow 3 includes methane, and a production of hydrogen and carbon oxides in the synthesis gas flow 7 from the methane of the energy carrier flow 3 takes place predominantly, and in some embodiments, substantially completely, by autothermic reforming with the oxygen flow 4 as the oxidant in the synthesis gas reactor assembly 6. In this case, predominantly means, for example, that at least 90% of the hydrogen and of the carbon oxides in the synthesis gas flow 7 is produced from the methane of the energy carrier flow 3 by autothermic reforming. The remaining fraction may trace back, for example, to the reforming activity of the pre-reformer 20 in the case of methane, which is basically low. Therefore, another mechanism, such as steam reforming, for obtaining a substantial amount of hydrogen and carbon oxides from the methane of the energy carrier flow 3 is excluded in this variant, so that effectively, only autothermic reforming takes place. In the first embodiment of the proposed method for the combined production of methanol 1 and ammonia 2, the synthesis gas flow 7 from the synthesis gas reactor assembly 6 substantially has a respective molar fraction of 44% hydrogen, 32% water, 16% carbon monoxide, 6% carbon dioxide and 1% methane, at a pressure of substantially 80 bars and a temperature of 1025° C.

With respect to obtaining the hydrogen-containing flow 10, in at least some embodiments, the residual gas flow 9 is at least partially fed to a pressure swing adsorption system (PSA) 21 for obtaining the hydrogen-containing flow 10. This PSA 21, which may be included in the system according to at least some embodiments, may also serve for draining a purge gas. If recycling the synthesis gas or of the carbon oxides can also be omitted in the methanol reactor assembly 8, recycling the hydrogen constitutes another possible variant. For example—as shown in FIG. 1—it may be that a first hydrogen partial flow 22a of the hydrogen-containing flow 10 is returned to the methanol reactor assembly 8, and there, in at least some embodiments, to the first reactor stage 16a. In this case, a pressure increase is not necessary, which is why in at least some embodiments, the first hydrogen partial flow 22a is substantially fed to the first reactor stage 16a with the pressure with which the hydrogen-containing flow 10 is obtained from the PSA 21. As is also shown in FIG. 1, a second hydrogen partial flow 22b of the hydrogen-containing flow 10 is then fed to the ammonia reactor assembly 11, in at least some embodiments.

It may be that the residual gas flow 9 is substantially completely fed to the PSA 21 for obtaining the hydrogen-containing flow 10. However, it may also be—as shown in FIG. 1—that a residual gas partial flow 23 of the residual gas flow 9 is fed to a desulfurization assembly 24a—which is included, for example, in the system according to at least some embodiments—for desulfurizing the carbon-containing energy carrier flow 3 by hydrogenation. With respect to the process, a saturation 24b may also be disposed between the desulfurization assembly 24a and the pre-reformer 20—as shown in FIG. 1.

The configuration of the ammonia reactor assembly 11 is basically arbitrary. In principle, the source of nitrogen for ammonia synthesis is equally arbitrary. First, in at least some embodiments, a nitrogen flow 25 obtained from the oxygen-producing assembly 5—i.e., in this case, from air separation—is also fed to the ammonia reactor assembly 11. The nitrogen, which is advantageously lacking in the synthesis gas and the methanol synthesis, may be fed back into the process flow in this manner.

The exemplary ammonia reactor assembly 11 shown in FIG. 1 has a first ammonia reactor stage 26a for synthesizing ammonia 2, which operates in a "once through" mode. The first ammonia reactor stage 26a operates in a low-pressure range—because, as described above, the compression is provided by the booster compressor 19. A first separation device 27a for separating ammonia 2 is followed by a main compressor 28 for a pressure increase to 150 bars in this case, downstream of which is a loop reactor assembly—i.e. a reactor assembly in circulatory operation.

In at least some embodiments, a second ammonia reactor stage 26b and a third ammonia reactor stage 26c for the respective synthesis of ammonia 2 are arranged serially downstream, with respect to the process, of the main compressor 28. In order to close the circulatory operation, the residual gas flow from a second separation device 27b for separating ammonia 2 is returned to the second ammonia reactor stage 26b by means of a recycling compressor 29. Due to the higher pressure in the second ammonia reactor stage 26b and the third reactor stage 26c, the conversion into ammonia in them takes place at a higher rate than in the first reactor stage 26a with the low pressure.

The system according to at least some embodiments serves for the methanol 1 and ammonia 2, namely in accordance with the method according to the proposal. The proposed system comprises the oxygen-producing assembly 5 for obtaining the oxygen flow 4, the synthesis gas reactor assembly 6 for obtaining the synthesis gas flow 7, which includes hydrogen and carbon oxides, from the carbon-containing energy carrier flow 3 and the oxygen flow 4, the methanol reactor assembly 8 for the partial conversion of the synthesis gas flow 7 into methanol 1 and for obtaining the residual gas flow 9, and the ammonia reactor assembly 11, to which the hydrogen-containing flow 10 is at least partially fed, which hydrogen-containing flow 10 was obtained from the residual gas flow 9, and in which ammonia reactor assembly 11 the hydrogen-containing flow 10 is at least partially converted into ammonia 2.

The system according to at least some embodiments is characterized in that, prior to the feeding to the methanol reactor assembly 8, the molar fraction of hydrogen in the synthesis gas flow 7 obtained from the synthesis gas reactor assembly 6 is increased in relation to the molar fraction of carbon oxides in an enrichment assembly 30. In at least some embodiments, the enrichment assembly includes the carbon dioxide scrubbing 12 and, alternatively or additionally, the shift conversion 14 as well as, if necessary, the control valve 15.

Features, properties and configurations of the system are apparent from the corresponding features, properties and configurations of the method for the combined production of methanol 1 and ammonia 2, or the method for producing a fuel, and vice versa.

Basically, in at least some embodiments, the methanol 1 produced in the method or the system can be put to any use, wherein temporary storage and transport of the methanol 1 may also be intended. However, the production of a fuel from the methanol 1 obtained in this manner may also be a suitable option.

Consequently, the proposed method for producing a fuel is characterized in that the fuel is obtained from methanol 1, which methanol 1 was produced in accordance with the proposed method for the combined production of methanol 1 and of ammonia 2.

In at least some embodiments, the fuel is produced by admixing the methanol 1 to motor gasoline, which was produced, for example, in a conventional manner. Consequently, a quantity of motor gasoline is already present, to which motor gasoline the methanol 1 is then admixed. In at least some embodiments, the fuel obtained in this manner has a volume fraction of 10% to 20%, or of substantially 15% of admixed methanol.

In at least some embodiments, the methanol 1 is processed into a derivative and the fuel is produced by admixing the derivative to the motor gasoline.

In at least some embodiments, it is provided that the methanol 1 is converted into the fuel. In this case, the methanol may on the one hand be converted into dimethyl ether (DME), which dimethyl ether is then used as a fuel according to one option. In at least some embodiments, however, the dimethyl ether is only an intermediate product in the further conversion into an aromatics-rich hydrocarbon mixture. At least some embodiments are characterized in that the methanol is converted, such as by means of zeolite catalysts, into an aromatics-rich hydrocarbon mixture via the intermediate product dimethyl ether, which hydrocarbon mixture, in at least some embodiments, forms the fuel.

In at least some embodiments, the methanol is directly converted by means of zeolite catalysts into an aromatics-rich hydrocarbon mixture. In this case, the hydrocarbon mixture may, on the one hand, form the fuel. On the other hand, the hydrocarbon mixture may be admixed to an existing fuel, wherein the resulting mixture then forms the produced fuel. It is also possible that the methanol is directly converted into the aromatics-rich hydrocarbon mixture by means of zeolite catalysts in a cooled fluidized-bed reactor.

Other variants of the proposed method for producing a fuel are apparent from the variants of the proposed method for the combined production of methanol 1 and ammonia 2 and from the variants of the proposed system for the combined production of methanol 1 and ammonia 2.

According to a first embodiment of the proposed method for the combined production of methanol 1 and ammonia 2, which is described further below, a natural-gas stream with a mass flow of, in total, 137,924.5 kg/h is provided at a temperature of 20° C. and a pressure of substantially 87 bars.

The synthesis gas flow 7 already described above, which is fed to the methanol reactor assembly 8 after shift conversion 13 and carbon dioxide scrubbing 12, has a mass flow of, in total, 241,818 kg/h. In addition, the first hydrogen partial flow 22a from the PSA 21 is fed to the methanol reactor assembly 8, wherein it substantially consists of 100% hydrogen at 43° C. and substantially 87 bars, and has a mass flow of 26,482 kg/h.

Directly when exiting the synthesis gas reactor assembly 6—and prior to being fed to a waste heat boiler, which is not shown here—the synthesis gas flow 7—as was already described above—substantially has a respective molar fraction of 44% hydrogen, 32% water, 16% carbon monoxide, 6% carbon dioxide and 1% methane, at 1025° C. and 80 bars. In this case, the mass flow in total is 523,265 kg/h. The difference in quantity between this mass flow and the mass flow of the synthesis gas flow 7 fed to the methanol reactor assembly 8 is substantially the result of, on the one hand, a washing process carried out by the carbon dioxide scrubbing 12 and, on the other hand, a considerable amount of water condensing out of the synthesis gas flow 7.

A carbon dioxide-containing flow, which has a molar fraction of almost 95% carbon dioxide and a mass flow of 76,163 kg/h, is obtained from carbon dioxide scrubbing 12.

Prior to being fed to the PSA 21, the residual gas flow 9 has a mass flow of 90,183 kg/h, wherein the residual gas flow 23 makes up about 50 kg/h of that.

The second hydrogen partial flow 22b from the PSA 21 is fed, together with the nitrogen flow 25, to the ammonia reactor assembly 11, and specifically to the first ammonia reactor stage 26a. In this case, the nitrogen flow 25 consists of more than 99% nitrogen and has a mass flow of 62,623 kg/h. The total gas flow supplied substantially has a respective molar fraction of 75% hydrogen and 25% nitrogen, with only 0.02% argon. The pressure is substantially 87 bars, at a temperature of 40° C. The mass flow, in total, is 63,972 kg/h. A mass flow of 60,390 kg/h ammonia is then obtained from the ammonia reactor assembly 11 as a whole.

A second embodiment of the proposed method for the combined production of methanol 1 and ammonia 2—in contrast to the first embodiment—aims for as balanced a production of methanol and ammonia as possible. Except for the differences described below of the second embodiment from the first embodiment of the proposed method for the combined production of methanol 1 and ammonia 2, the statements given with regard to the first embodiment apply; for example, the same information regarding the natural-gas stream as in the first embodiment applies.

In this case, the carbon-containing energy carrier flow fed to the synthesis gas reactor assembly 6 from the pre-reformer 20—apart from a slightly greater mass flow of 371,748 kg/h—substantially has the temperature and pressure conditions and the molar fractions described with respect to the first embodiment. The information from the first embodiment basically also applies to the synthesis gas flow 7 from the synthesis gas reactor assembly 6, with the mass flow amounting to 523,277 kg/h in total.

For the purpose of the above-mentioned balanced production, the control valve 15 is set such that—in each case at a pressure of substantially 77 bars and a temperature of 320° C.—a partial flow 13 with a mass flow of 209,311 kg/h is branched off to shift conversion 14, wherein a mass flow 313,966 kg/h is made to bypass the shift conversion 14 by the control valve 15. Both the partial flow 13 and the remaining bypassed synthesis gas flow 7 in this case substantially have a respective molar fraction of 44% hydrogen, 32% water, 16% carbon monoxide, 6% carbon dioxide, 1% methane and less than 1% nitrogen.

The synthesis gas flow 7 fed to the methanol reactor assembly 8 after carbon dioxide scrubbing 12, with a mass flow of a total of 185,661 kg/h, substantially has a respective molar fraction of 77% hydrogen, 16% carbon monoxide, 2% carbon dioxide, 2% methane, 2% water and 1% nitrogen. Therefore, compared with the first embodiment, the fraction of hydrogen is increased in relation to the fraction of carbon monoxide. No first hydrogen partial flow 22a is returned in at least some embodiments.

The carbon dioxide-containing flow from carbon dioxide scrubbing 12, with a molar fraction of also almost 95% carbon dioxide, has a mass flow of 171,906 kg/h.

This results in a residual gas flow 9—again prior to being fed to the pressure swing adsorption system 21—with a respective molar fraction of substantially 87% hydrogen, 4% carbon monoxide, 2% carbon dioxide, 4% methane, 1% water and 2% nitrogen, and with a mass flow of 66,893 kg/h, wherein the residual gas partial flow 23 again makes up about 50 kg/h.

In this case, the nitrogen flow 25 has a mass flow of 89,430 kg/h. The gas flow fed in total to the ammonia reactor assembly 11 differs from the first embodiment only in its mass flow of 108,717 kg/h in total, wherein a mass flow of 105,067 kg/h ammonia is then obtained from the ammonia reactor assembly 11 as a whole.

A mass flow of approx. 60,318 kg/h methanol 1 is obtained from the first condensation stage 18a. A mass flow of, in total, about 46,211 kg/h methanol 1 is obtained from the second condensation stage 18b and the scrubber device 18d, which, together with the methanol 1 from the first condensation stage 18a, adds up to a mass flow of about 106,529 kg/h methanol 1, and thus corresponds to only about ⅔ of the corresponding value of the first embodiment. A pure methanol flow substantially consisting of methanol with a mass flow of 106,332 kg/h is then obtained from the distillation device 18c. More ammonia, and instead less methanol, is recognizably produced in the second embodiment.

A third embodiment of the proposed method for the combined production of methanol 1 and ammonia 2, which is described below, again aims for a production of methanol, which may be emphasized over the production of ammonia in at least some embodiments. In other words, there is an over-emphasis on the production of methanol over the production of ammonia.

Again, the statements regarding the first embodiment of the method according to the proposal may apply—unless otherwise stated.

The natural-gas stream is the identical. The carbon-containing energy carrier flow 3 fed to the synthesis gas reactor assembly 6 from the pre-reformer 20 has a mass flow of 371,734 kg/h. The synthesis gas flow 7 from the synthesis gas reactor assembly 6 has a mass flow of, in total, 523,266 kg/h.

A branching-off by means of the control valve 15 takes place. In at least some embodiments, a partial flow 13 with a mass flow of 52,326 kg/h is branched off to shift conversion 14, and a mass flow of 470,939 kg/h is made to bypass the shift conversion 14 by the control valve 15, wherein the pressure and temperature conditions as well as the respective molar fractions as in the second embodiment of the method apply.

The synthesis gas flow 7 fed to the methanol reactor assembly 8 after carbon dioxide scrubbing 12 has a mass flow of a total of 227,778 kg/h and substantially a respective molar fraction of 70% hydrogen, 22% carbon monoxide, 2% carbon dioxide, 2% methane, 2% water and 1% nitrogen.

The carbon dioxide-containing flow from carbon dioxide scrubbing 12, with a molar fraction of, again, almost 95% carbon dioxide, has a mass flow of 100,098 kg/h.

This results in a residual gas flow 9, prior to being fed to the pressure swing adsorption system 21, with a respective molar fraction of substantially 90% hydrogen, 4% carbon monoxide, 1% carbon dioxide, 2% methane, 1% water and 1% nitrogen. The mass flow amounts to 85,447 kg/h, wherein about 50 kg/h are attributable to the residual gas partial flow 23.

The nitrogen flow 25 has a mass flow of 41,450 kg/h. The gas flow fed in total to the ammonia reactor assembly 11 has a mass flow of 50,390 kg/h in total, wherein a mass flow of 46,835 kg/h ammonia is then obtained from the ammonia reactor assembly 11 as a whole.

A mass flow of approx. 86,300 kg/h methanol 1 is obtained from the first condensation stage 18a. A mass flow of, in total, about 65,586 kg/h methanol 1 is obtained from the second condensation stage 18b and the scrubber device 18d, which, together with the methanol 1 from the first condensation stage 18a, adds up to a mass flow of about 151,886 kg/h methanol 1. A pure methanol flow substantially consisting of methanol with a mass flow of 151,670 kg/h is then obtained from the distillation device 18c.

While the above describes certain embodiments, those skilled in the art should understand that the foregoing description is not intended to limit the spirit or scope of the present disclosure. It should also be understood that the embodiments of the present disclosure described herein are merely exemplary and that a person skilled in the art may make any variations and modification without departing from the spirit and scope of the disclosure. All such variations and modifications, including those discussed above, are intended to be included within the scope of the disclosure.

The invention claimed is:

1. A method for the combined production of methanol and of ammonia comprising:
feeding a carbon-containing energy carrier flow and an oxygen flow from an oxygen-producing assembly to a synthesis gas reactor assembly, wherein an oxygen fraction of the oxygen flow is at least about 80% of the oxygen flow,
obtaining a synthesis gas flow containing hydrogen and carbon oxides from the synthesis gas reactor assembly,
feeding the synthesis gas flow to a methanol reactor assembly having a first reactor stage configured for the synthesis of methanol and a second reactor stage configured for the synthesis of methanol and at least partially converting the synthesis gas flow into methanol therewith, wherein the step of feeding the synthesis gas flow includes (i) feeding the synthesis gas flow to the first reactor stage, (ii) feeding an unreacted residual gas from the first reactor stage to a booster compressor, (iii) increasing a pressure of the unreacted residual gas with the booster compressor, and (iv) feeding the unreacted residual gas to the second reactor stage,
obtaining a residual gas flow comprising methanol from the methanol reactor assembly,
obtaining a hydrogen-containing flow from the residual gas flow including feeding at least part of the residual gas flow to a pressure swing adsorption system (PSA),
feeding at least part of the hydrogen-containing flow to an ammonia reactor assembly,
at least partially converting the hydrogen-containing flow into ammonia in the ammonia reactor assembly, and
performing an enrichment step, including:
increasing a molar fraction of hydrogen in the synthesis gas flow obtained from the synthesis gas reactor assembly relative to a molar fraction of carbon oxides therein prior to the step of feeding the synthesis gas flow to the methanol reactor assembly.

2. The method according to claim 1, wherein the enrichment step further comprises at least partially removing carbon dioxide from the synthesis gas flow.

3. The method according to claim 1, wherein the enrichment step further comprises feeding at least one partial flow of the synthesis gas flow to a shift conversion, and at least partially converting carbon monoxide in the synthesis gas flow into hydrogen and carbon dioxide by a reaction with water vapor.

4. The method according to claim 3, further comprising the shift conversion substantially exclusively performing a high-temperature water-gas shift reaction.

5. The method according to claim 1, comprising substantially completely converting carbon monoxide in the synthesis gas flow fed to the methanol reactor assembly into methanol, whereby a molar fraction of carbon monoxide in the residual gas flow is no more than about 4%.

6. The method according to claim 1, wherein the unreacted residual gas fed to the second reactor stage includes substantially all unreacted carbon oxides exited from the first reactor stage.

7. The method according to claim 1, wherein the residual gas flow includes substantially all unreacted carbon oxides exited from the second reactor stage.

8. The method according to claim 1, further including separating methanol synthesized in the first reactor stage and obtaining the unreacted residual gas from the first reactor stage using a first condensation stage downstream from the first reactor stage.

9. The method according to claim 1, wherein the step of obtaining the synthesis gas flow includes performing autothermic reforming with the oxygen flow as an oxidant.

10. The method according to claim 9, wherein the carbon-containing energy carrier flow includes methane, and further comprising providing said hydrogen and carbon oxides in the synthesis gas flow from the methane of the carbon-containing energy carrier flow at least in part by performing autothermic reforming with the oxygen flow as oxidant in the synthesis gas reactor assembly.

11. The method according to claim 1, further comprising feeding part of the residual gas flow to a desulfurization assembly and desulfurizing therewith the carbon-containing energy carrier flow by hydrogenation.

12. A method for producing a fuel, comprising:
  producing methanol by:
    feeding a carbon-containing energy carrier flow and an oxygen flow from an oxygen-producing assembly to a synthesis gas reactor assembly, wherein an oxygen fraction of the oxygen flow is at least about 80% of the oxygen flow,
    obtaining a synthesis gas flow containing hydrogen and carbon oxides from the synthesis gas reactor assembly,
    performing an enrichment step including increasing a molar fraction of hydrogen in the synthesis gas flow relative to a molar fraction of carbon oxides; and
    feeding the enriched synthesis gas flow to a methanol reactor assembly having a first reactor stage configured for the synthesis of methanol and a second reactor stage configured for the synthesis of methanol and at least partially converting the enriched synthesis gas flow into methanol therewith, wherein the step of feeding the enriched synthesis gas flow includes (i) feeding the enriched synthesis gas flow to the first reactor stage, (ii) feeding an unreacted residual gas from the first reactor stage to a booster compressor, (iii) increasing a pressure of the unreacted residual gas with the booster compressor, and (iv) feeding the unreacted residual gas to the second reactor stage, and
  producing fuel using the methanol.

13. A system for the combined production of methanol and of ammonia, comprising
  an oxygen-producing assembly configured to provide an oxygen flow, wherein an oxygen fraction of the oxygen flow is at least about 80% of the oxygen flow,
  a synthesis gas reactor assembly configured to provide a synthesis gas flow containing hydrogen and carbon oxides from a carbon-containing energy carrier flow and said oxygen flow,
  a methanol reactor assembly configured to at least partially convert the synthesis gas flow into methanol and to provide a residual gas flow comprising methanol, wherein the methanol reactor includes a first reactor stage configured for the synthesis of methanol, a second reactor stage configured for the synthesis of methanol, and a booster compressor configured to increase a pressure of unreacted residual gas from the first reactor stage prior to feeding thereof to the second reactor stage,
  a pressure swing adsorption system configured to generate a hydrogen-containing flow from at least part of the residual gas flow,
  an ammonia reactor assembly configured to receive the hydrogen-containing flow generated from the residual gas flow, and to at least partially convert the hydrogen-containing flow into ammonia, and
  an enrichment assembly configured to increase a molar fraction of hydrogen in the synthesis gas flow relative to a molar fraction of carbon oxides therein.

* * * * *